(12) United States Patent
Moshe (10) Patent No.: US 6,694,048 B2
(45) Date of Patent: Feb. 17, 2004

(54) METHOD FOR GENERATING INTRA-PARTICLE MORPHOLOGICAL CONCENTRATION/DENSITY MAPS AND HISTOGRAMS OF A CHEMICALLY PURE PARTICULATE SUBSTANCE

(75) Inventor: Danny S. Moshe, Kiryat Ono (IL)

(73) Assignee: Green Vision Systems Ltd., Tel Aviv (IL)

( * ) Notice: Subject to any disclaimer, the term of this patent is extended or adjusted under 35 U.S.C. 154(b) by 0 days.

(21) Appl. No.: 10/240,238

(22) PCT Filed: Apr. 19, 2001

(86) PCT No.: PCT/IL01/00366
§ 371 (c)(1),
(2), (4) Date: Sep. 30, 2002

(87) PCT Pub. No.: WO01/84106
PCT Pub. Date: Nov. 8, 2001

(65) Prior Publication Data
US 2003/0206649 A1 Nov. 6, 2003

Related U.S. Application Data
(60) Provisional application No. 60/198,556, filed on Apr. 20, 2000.

(51) Int. Cl.[7] .................................................. G06K 9/00
(52) U.S. Cl. ...................... 382/133; 382/128; 382/168; 382/170; 382/255; 382/302; 702/27
(58) Field of Search ................................ 382/133, 128, 382/168, 170, 255, 302; 377/10, 13; 128/922; 250/455.11, 461.1, 366, 459.1; 356/39, 318; 702/27; 430/435

(56) References Cited

U.S. PATENT DOCUMENTS

| 5,568,571 | A | * | 10/1996 | Willis et al. ................. 382/254 |
| 5,880,830 | A | | 3/1999 | Schecter |
| 6,091,843 | A | | 7/2000 | Horesh et al. |
| 6,137,899 | A | * | 10/2000 | Lee et al. .................... 382/133 |
| 6,208,749 | B1 | * | 3/2001 | Gutkowicz-Krusin et al. ... 382/128 |
| 6,438,261 | B1 | | 8/2002 | Moshe et al. |
| 6,584,413 | B1 | * | 6/2003 | Keenan et al. ................. 702/28 |
| 2002/0097388 | A1 | * | 7/2002 | Raz .............................. 356/39 |
| 2003/0049867 | A1 | * | 3/2003 | Selifonov et al. ........... 436/518 |

* cited by examiner

Primary Examiner—Bhavesh M. Mehta
Assistant Examiner—Barry Choobin
(74) Attorney, Agent, or Firm—G. E. Ehrlich Ltd.

(57) ABSTRACT

An method for generating intra-particle morphological concentration/density maps and histograms of a chemically pure particulate substance. Spectral imaging, in general, and focus-fusion multi-layer spectral imaging, in particular, combined with pattern recognition classification analysis are performed on individual particles for forming sets of single-particle spectral fingerprint data, characterized by single-particle spectral fingerprint spectra. Spectral shifts are identified in the single-particle spectral fingerprint data, for forming intra-particle region groups featuring sub-sets of intra-particle spectral fingerprint pattern data, each characterized by an intra-particle spectral fingerprint pattern spectrum. Each intra-particle region group is associated with different types of intra-particle morphological regions, where each region type is associated with a surface concentration value and a density value of the chemically pure substance in that imaged particle, for forming intra-particle morphological concentration/density data, which is used for generating an intra-particle morphological concentration/density map. A morphological concentration/density histogram, or frequency distribution, is generated from the intra-particle morphological concentration/density data, for illustrating global morphological distribution of concentration, and density of the chemically pure substance throughout the entire multi-particle substance.

27 Claims, 4 Drawing Sheets

MCD [p1: R1, SC(R1), D(R1): R2, SC(R2), D(R2):
R3, SC(R3), D(R3): R4, SC(R4), D(R4)]

METHOD FOR GENERATING INTRA-PARTICLE MORPHOLOGICAL CONCENTRATION/DENSITY MAPS AND HISTOGRAMS OF A CHEMICALLY PURE PARTICULATE SUBSTANCE

This application claims benefit of provisional application 60/198,556 filed Apr. 20, 2000.

FIELD AND BACKGROUND OF THE INVENTION

The present invention relates to a method for determining physicochemical characteristics of a particulate substance and, more particularly, to a method for generating intra-particle morphological concentration/density maps and histograms of a chemically pure particulate substance by spectral imaging of individual particles of the chemically pure particulate substance and analyzing the spectral images using pattern recognition classification analysis.

In the highly regulated biopharmaceutical industry, an important stage during research and development of a new therapeutic product such as a drug, high-performance chemical, or micro-organism, featuring at least one chemically pure particulate substance either in the raw material(s) and/or in the eventual finished product formulated as a tablet, capsule, caplet, or loose powder, involves extensive and well documented laboratory analytical testing of the physicochemical properties and characteristics of each chemically pure particulate substance. Hereinafter, the term 'chemically pure particulate substance' refers to particulate substance featuring one, or a combination of several, chemically pure individual chemical compounds, where the chemically pure particulate substance is typically heterogeneous with respect to physical location or morphological distribution of the concentration and/or density of the at least one chemically pure compound throughout a given sized sample of the chemically pure particulate substance.

Information about the physicochemical properties of each chemically pure particulate substance are needed in a later stage for performing pharmacodynamical studies, involving metabolic and efficacy studies of the therapeutic product when ingested by an animal or human during pre-clinical and clinical studies. Metabolic information about the therapeutic product is needed for designing and evaluating efficacy studies, where the effectiveness of the therapeutic product for performing the indicated therapeutic function in a subject is measured. Ultimately, information and data from the efficacy studies are used for establishing the final formulation and recommended dosage levels of the new therapeutic product for dispensing to the consumer market. Correspondingly, data and information about the final formulation are used for establishing standardized quality control parameters and criteria for full-scale manufacturing of the new therapeutic product.

Full-scale manufacturing of such a new or current, therapeutic product, involves extensive and well documented standardized quality control testing of each chemically pure particulate raw material and/or the chemically pure particulate finished product, according to established quality control and quality assurance parameters and criteria. Similar to the research and development stages of such a product, this involves laboratory analytical testing and classification of the physicochemical properties and characteristics of each chemically pure particulate substance relating to the therapeutic product.

Laboratory analytical testing of such a particulate substance, during research and development stages or during routine finished product quality control testing, typically includes measuring and determining concentration(s) and/or density(ies), and morphological properties and characteristics such as particle size and particle geometry, shape, or porosity distributions of a sample of the chemically pure particulate substance, in a statistically meaningful manner. Typically, such laboratory testing also includes measuring and determining dissolution properties of each applicable or selected chemically pure particulate substance. Dissolution testing provides data and information about the kinetics and thermodynamics of dissolution of a given chemically pure particulate substance in a variety of solvents. As indicated above, such detailed information about the physicochemical properties of each chemically pure particulate substance is valuable and used for either understanding, classifying, or quality control testing pharmacodynamical behavior of the therapeutic product.

It is commonly known in the field of physical chemistry of particulate matter that dissolution properties and behavior of a particle, and therefore, of a sample of particulate substance featuring a plurality of particles, in a liquid medium, either in-vitro or in-vivo, are closely related to and functions of morphological properties and characteristics such as particle size, geometry or shape, and porosity distributions, and, concentration and/or density, of the particulate substance. Thus, measuring and determining data and information about the latter particle properties and characteristics, are useful for highly accurately and reproducibly determining, understanding, classifying, and testing dissolution properties and behavior of the particulate substance. This relationship is clearly applicable to laboratory analytical testing of chemically pure particulate substances extensively performed by the biopharmaceutical industry, as described above.

There are extensive prior art methods, devices, and systems, relating to accurately and reproducibly measuring and determining morphological properties and characteristics of a particulate substance, where these are typically based on imaging the particulate substance. Spectral imaging is currently a widely used technique for imaging particles. In spectral imaging, a particulate substance is affected in a way, for example, excitation by incident ultraviolet light upon the substance, which causes the substance to emit light featuring an emission spectra. Emitted light is recorded by an instrument such as a scanning interferomneter that generates a set of interferogram images, which in turn are used to produce a spectral image, also referred to as a cube image, of the substance. Each cube (spectral) image is a three dimensional data set of voxels (volume of pixels) in which two dimensions are spatial coordinates or position, (x, y), in the substance and the third dimension is the wavelength, ($\lambda$), of the imaged (emitted) light of the substance, such that coordinates of each voxel in a spectral image or cube image may be represented as (x, y, $\lambda$). Any particular wavelength, ($\lambda$), of imaged light of the substance is associated with a set of cube images or spectral fingerprints of the substance in two dimensions, for example, along the x and y directions, whereby voxels having that value of wavelength constitute the pixels of a monochromatic image of the substance at that wavelength. Each cube image, featuring a range of wavelengths of imaged light of the substance is analyzed to produce a two dimensional map of the chemical composition, or of some other physicochemical property of the substance, for example, particle size distribution.

An example of a method and system for real-time, on-line chemical analysis of particulate substances, for example, polycyclic aromatic hydrocarbon (PAH) particles in aerosols, in which the PAH substance is excited to emit light, for example fluorescence, is that of U.S. Pat. No. 5,880,830, issued to Schechter, and manufactured by Green Vision Systems Ltd. of Tel Aviv, Israel, the teachings of which are incorporated by reference for all purposes as if fully set forth herein. In the disclosed method, spectral imaging techniques are implemented to acquire an image and analyze the properties of fixed position PAH particles. As part of this method, air is sampled by means of a high volume pump sucking a large volume of air featuring aerosol contaminated with PAH particles onto a substrate, followed by on-line imaging and scene analysis of the stationary particles.

A method of calibration and real-time analysis of particles is described in U.S. Pat. No. 6,091,843, to Moshe et al., the teachings of which are incorporated by reference for all purposes as if fully Set forth herein. The method described, is based on using essentially the same system of U.S. Pat. No. 5,880,830, for acquiring spectral images of static particles on a filter. In brief, there is disclosed a method of analyzing particles for the presence of chemical or biological species, by spectral imaging of the particles. The output of the image acquisition is, for each imaged portion of a two-dimensional surface host to the particles, a set of images, each image at a different wavelength. These images are digitized and analyzed by standard image processing methods to produce, for each imaged portion of the two-dimensional surface, spectral images of targets.

In the disclosure of U.S. Pat. No. 6,091,843, targets are identified in static particle images and are classified according to morphology type and spectrum type. Each target is assigned a value of an extensive property. A descriptor vector is formed, where each element of the descriptor vector is the sum of the extensive property values for one target class. The descriptor vector is transformed, for example, to a vector of mass concentrations of chemical species of interest, or of number concentrations of biological species of interest, using a relationship determined in the calibration procedure. In the calibration procedure, spectral images of calibration samples of static particles having known composition are acquired, and empirical morphology types and spectrum types are inferred from the spectral images. Targets are identified in the calibration spectral images, classified according to morphology type and spectrum type, and assigned values of an extensive property. For each calibration sample, a calibration descriptor vector and a calibration concentration vector is formed. A collective relationship between the calibration descriptor vectors and the calibration concentration vectors is found using chemometric methods.

In conventional scene analysis using the above described methods and systems for spectral imaging of individual particles, for example, for each scene, there is auto-focusing, where a best focal position is determined for use in analyzing or classifying particle properties. For some scenes, this is possible, and a focused image may be obtained in an automatic manner. Typically, an auto-focus module is coupled with a computer controlled mechanism that automatically changes the focal position, by moving along an axis parallel to the optical axis of the imaging or focusing sensor, thereby enabling identification of a good focal position. For other scenes, a good focal position is not guaranteed to exist and further image processing based on focus-fusion methodology is required.

When focused images of spatially varying or depth dependent scenes can not be generated by using such auto-focus electromechanical means, such that single focal positions can not be identified, focused representations of the scenes can be constructed by combining or fusing selected portions of several defocused images of each scene. This process is referred to as focus-fusion imaging, and the resulting images of such processing are referred to as a focus-fusion images. Defocused images, for example, those acquired during auto-focusing, are fused together such that each target in a given scene is in correct focus. Scene targets are detected by analyzing either focused images, if they exist, or focus-fusion images.

Spectral imaging of spatially varying, depth dependent, or multi-layered samples of particles is not described in the above referenced methods and systems. Imaging and image analysis of a random single two-dimensional layer of a particulate substance are ordinarily straightforward. However, multi-layer imaging and image analysis of depth dependent particulate substances, for example, multi-layered dry particles, or particles in a frozen or immobilized suspension, are substantially more complex. Nevertheless, there are instances where it is necessary to obtain property and classification information of depth dependent particulate substances, in-situ, for example, as part of sampling an industrial process. More often than not, images obtained of such particulate substances are defocused, and require special image processing techniques, such as focus-fusion, for obtaining useful information about the substances.

Additionally, the above described disclosures feature useful methods and systems for acquiring and analyzing spectral images of particles, but are limited to identifying and quantifying the presence of species on particles, where the species are typically considered particle impurities, and therefore, there is no description of spectral imaging and analysis of a chemically pure particulate substance. Furthermore, there is no description of a method for applying the described pattern recognition classification procedures for analyzing intra-particle spectral images of individual particles, where the concentration and/or density of the chemical substance in the host particles, separate from impurity species concentration, are spectrally related to particle morphological characteristics such as particle size and/or shape.

Recently, it has been disclosed that scene analysis by applying focus-fusion methodology to defocused images acquired by multi-layer spectral imaging of depth dependent particulate substances is quite useful for detecting and classifying in-situ physicochemical information of the particles, such as particle size distribution, morphological features, including structure, form, and shape characteristics, and chemical composition, which ideally involve multi layer three-dimensional image analysis. In U.S. Pat. No. 6,438,761, filed Dec. 4, 2000, entitled "Method For In-situ Focus-fusion Multi-layer Spectral Imaging And Analysis Of Particulate Samples", which is a Continuation-in-Part of U.S. Pat. No. 6,173,703, filed Jun. 1, 1999, of same title, which is a Continuation-in-Part of U.S. patent application Ser. No. 09/146,361 (now U.S. Pat. No. 6,091,843, previously summarized above), the teachings of which are incorporated by reference for all purposes as if fully set forth herein, there is disclosed a method for in-situ focus-fusion multi-layer spectral imaging and analysis of depth dependent particulate substances.

In U.S. Pat. No. 6,438,261, a unique method of focus-fusion is applied to focused and defocused images acquired from multi-layer spectral imaging of a depth dependent particulate substance, in order to construct focused fused cube (spectral) image representations of the imaged particles, thereby generating a focused image of essentially each particle in a sample of the substance. The disclosed method features the use of a uniquely defined and calculated focus-fusion factor parameter, $F_b$, which combines (1) empirically determined particle physicochemical information and parameters relating to (i) particle chemical composition and associated chemistry, and relating to (ii) particle morphology such as particle size and shape, with (2) empirically determined particle spectral information and parameters such as (i) pixel intensity, (ii) signal-to-noise ratio (S/N), (iii) image sharpness, (iv) spectral distances, and (v) spectral fingerprints relating to spectral emission patterns of individual particles. The focus-fusion factor parameter, $F_b$, is used in critical steps of image detection, image analysis, and in algorithms for classification of particle characteristics. This uniquely determined parameter enables achievement of high levels of accuracy and precision in detection and classification of the substance, in general, and of the individual particles, in particular.

The disclosed method includes collecting and analyzing physicochemical and multi-layer spectral data relating to the particles in the sample, including mapping of three-dimensional positions of particles, particle sizes, and characteristics of particle emission spectra. Scene information, in the form of spectral fingerprints, used in the analysis of focus-fusion of the multi-layer spectral images is further processed in order to generate relevant in-situ physicochemical information of the particles, such as particle size distribution, morphological features, including structure, form, and shape characteristics, and chemical composition. The focus-fusion multi-layer spectral image analysis includes a sophisticated classification procedure for extracting, on-line, useful information relating to particle properties and characteristics needed for generating a report applicable to monitoring or controlling an industrial process.

According to that disclosure, the method of focus-fusion multi-layer spectral imaging and analysis of depth dependent particulate samples can be applied to a sample of chemically pure particles. However, each described alternative procedure for analyzing the data of the fused cube images of the particles, is with respect to either an individual particle as the simplest unit or object of imaging and analysis, or with respect to a sample of many such particles. There is no description with respect to variation of intra-particle properties or characteristics, and consequently, there is no relating variation of intra-particle properties or characteristics such as intra-particle concentration and/or density to intra-particle focus-fusion spectral image data.

In actuality, it turns out, especially with regard to laboratory analytical testing of particulate materials, as currently practiced by pharmaceutical, biotechnology, and chemical industries, that at a more detailed level, measuring and determining physicochemical properties and characteristics of a sample of particulate substance, such as of a chemically pure particulate substance, at the particle level, are insufficient for highly accurately and reproducibly relating the physicochemical data and information to results of pharmacodynamical studies of the particulate substance. This phenomenon is particularly evident where a chemically pure particulate substance is heterogeneous with respect to intra-particle and/or inter-particle morphological distribution of the concentration and/or density of at least one chemically pure compound throughout the chemically pure particulate substance.

There is thus a need for, and it would be highly advantageous to have a method for generating intra-particle morphological concentration/density maps and histograms of a chemically pure particulate substance by spectral imaging, in general, and, by focus-fusion multi-layer spectral imaging, in particular, of individual particles of the chemically pure particulate substance and analyzing the spectral images using pattern recognition classification analysis.

SUMMARY OF THE INVENTION

The present invention relates to a method for generating intra-particle morphological concentration/density maps and histograms of a chemically pure particulate substance by spectral imaging, in general, and, by focus-fusion multi-layer spectral imaging, in particular, of individual particles of the chemically pure particulate substance and analyzing the spectral images using pattern recognition classification analysis.

Thus, according to the present invention there is provided a method for generating intra-particle morphological concentration/density maps and histograms of a chemically pure particulate substance, comprising the steps of: (a) acquiring a set of spectral images by a spectral imaging system for each of a number of particles of the chemically pure particulate substance having a plurality of the particles; (b) performing pattern recognition classification analysis on each set of the acquired spectral images for each imaged particle, for forming a number of sets of single-particle spectral fingerprint data; (c) identifying at least one spectral shift in each set of single-particle spectral fingerprint data associated with each imaged particle, for forming an intra-particle region group featuring a plurality of sub-sets of intra-particle spectral fingerprint pattern data, where selected data elements in each sub-set are shifted relative to corresponding data elements in each remaining sub-set in the same intra-particle region group; (d) forming a set of intra-particle morphological concentration/density data relating to each imaged particle from each intra-particle region group; (e) generating each of the intra-particle morphological concentration/density maps from each set of the intra-particle morphological concentration/density data; and (f) generating each of the morphological concentration/density histograms from a plurality of the sets of the intra-particle morphological concentration/density data, for illustrating a statistically based global morphological distribution of surface concentration and density throughout the chemically pure particulate substance.

According to another aspect of the present invention, there is provided a method for identifying intra-particle morphological distribution of surface concentration and density of a chemically pure particulate substance, comprising the steps of: (a) acquiring a set of spectral images by a spectral imaging system for each of a number of particles of the chemically pure particulate substance having a plurality of the particles; (b) performing pattern recognition classification analysis on each set of the acquired spectral images for each imaged particle, for forming a number of sets of single-particle spectral fingerprint data; (c) identifying at least one spectral shift in each set of single particle spectral fingerprint data associated with each imaged particle, for forming an intra-particle region group featuring a plurality of sub-sets of intra-particle spectral fingerprint pattern data, where selected data elements in each sub-set are shifted relative to corresponding the data elements in each remaining sub-set in the same intra-particle region group; (d) forming a set of intra-particle morphological concentration/density data relating to each imaged particle from each intra-particle region group; and (e) forming a plurality of intra-particle morphological region types from each set of the intra-particle morphological concentration/density data, where each intra-particle morphological region type is associated with a different value of the surface concentration and a different value of the density of the chemically pure particulate substance, thereby identifying the intra-particle morphological distribution of the surface concentration and density of the chemically pure particulate substance.

In the method of the present invention, spectral imaging, in general, and focus-fusion multi-layer spectral imaging, in particular, combined with appropriate pattern recognition classification analysis are performed on a number of individual particles of a plurality of particles of the chemically pure particulate substance, for forming a plurality of sets of single-particle spectral fingerprint data, where each set is characterized by a single-particle spectral fingerprint spectrum. This information is stored in a single-particle scenario database.

In each set of single-particle spectral fingerprint data, spectral shifts are identified, for forming an intra-particle region group featuring a plurality of sub-sets of intra-particle spectral fingerprint pattern data. Each sub-set is characterized by an intra-particle spectral fingerprint pattern spectrum, which is associated with the same single-particle spectral fingerprint spectrum as the other intra-particle spectral fingerprint pattern spectra of the other sub-sets in the same intra-particle region group. This information is stored in an intra-particle scenario database.

Each intra-particle region group featuring the plurality of sub-sets of intra-particle spectral fingerprint pattern data is associated with a plurality of intra-particle morphological region type identifiers, where each intra-particle morphological region type identifier is associated with a surface concentration value and a density value of the chemically pure substance in that imaged particle, for forming a set of intra-particle morphological concentration/density data, stored in an intra-particle morphological concentration/density database.

For each particle, the set of intra-particle morphological concentration/density data is used for generating an intra-particle morphological concentration/density map for illustrating local, intra-particle, morphological distribution of surface concentration and density of the chemically pure substance throughout the imaged particle. For that number of imaged and analyzed particles of the plurality of particles of the particulate substance, a morphological concentration/density histogram, or frequency distribution, is generated from a plurality of sets of the intra-particle morphological concentration/density data, for illustrating a statistically based global morphological distribution of concentration and density throughout the entire chemically pure particulate substance.

The method and system of the present invention, compared to currently used methods and systems, provide new capabilities for effectively and efficiently determining and classifying intra-particle morphological concentration/density data and related information, for application to the pharmaceutical, biotechnology, chemical, and other industries requiring intra-particle physicochemical analysis and characterization of a chemically pure particulate substance.

The method of the present invention is generally applicable to spectral imaging of chemically pure particulate substances, and, is particularly applicable to multi-layer focus-fusion spectral imaging, multi-layer scene analysis, and multi-layer physicochemical characterization of chemically pure particulate substances featuring depth dependency, where layer or depth variations of imaged samples of powders, frozen suspensions of powders, biological specimens, or other multi-layered chemically pure particulate samples are typically large compared to differential imaging distances, and where there is a need for effectively and efficiently determining and classifying intra-particle morphological concentration/density data arid related information of the chemically pure particulate substance. The present invention is especially well suited for analyzing spectral images of chemically pure particulate substances of medicines, for example, medicines containing both chemically pure active ingredients and chemically pure inactive ingredients, whereby there is distinguishing and characterizing physicochemical properties and features of the active and inactive ingredients.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention relates to a method for determining physicochemical characteristics of a particulate substance and, more particularly, to a method for generating intra-particle morphological concentration/density maps and histograms of a chemically pure particulate substance by spectral imaging, in general, and, by focus-fusion multi-layer spectral imaging, in particular, of individual particles of the chemically pure particulate substance and analyzing the spectral images using pattern recognition classification analysis.

As previously indicated above, the term 'chemically pure particulate substance' refers to particulate substance featuring at least one, or a combination of several, chemically pure individual chemical compounds, where the chemically pure particulate substance is typically heterogeneous with respect to physical location or morphological distribution of the concentration and/or density of the at least one chemically pure compound throughout a given sized sample of the chemically pure particulate substance. Exemplary types of a chemically pure particulate substance are a powder, a powder mixture, a medicinal powder featuring at least one active ingredient and at least one inactive ingredient, a frozen suspension of a powder, and a biological specimen. According to the actual type of chemically pure particulate substance subjected to the spectral imaging, physicochemical properties and characteristics of the particles of the chemically pure particulate substance are either independent or dependent upon layer or depth into each particle.

It is to be understood that the invention is not limited-in its application to the details of the order or sequence of steps of operation or implementation, or, construction, arrangement, and composition of the components of exemplary analytical instrumentation and related equipment, set forth in the following description, drawings, or examples. The invention is capable of other embodiments or of being practiced or carried out in various ways. Also, it is to be understood that the phraseology and terminology employed herein are for the purpose of description and should not be regarded as limiting.

Steps, sub-steps, components, operation, and implementation of the method for generating intra-particle morphological concentration/density maps and histograms of a chemically pure particulate substance by spectral imaging, in general, and, by focus-fusion multi-layer spectral imaging, in particular, of individual particles of the chemically pure particulate substance and analyzing the spectral images using pattern recognition classification analysis, according to the present invention are better understood with reference to the following description and the accompanying drawings.

While searching for a method of applying spectral imaging, in general, and, focus-fusion multi-layer spectral imaging (focusing on a single particle layer or a multiple of particle layers, where each layer corresponds to one spectral image cube per field-of-view of a spectral imaging device), in particular, combined with pattern recognition classification analysis for improving physicochemical characterization of a sample of a chemically pure, but morphologically heterogeneous, particulate substance, it was unexpectedly determined at the single particle level, that each spectrum, in each group of spectra associated with a set of imaged targets, or 'Blobs' (the terms 'targets' and 'Blobs' are defined and described in detail in previously cited U.S. patent application Ser. No. 09/727,753, above), within the same particle and assigned the same spectral fingerprint of that particle, features spectral parameters, for example, emission wavelength and/or emission intensity or amplitude, shifted with respect to the corresponding same spectral parameters of each of the remaining spectra of that same group of spectra. Accordingly, each spectrum in each such group of spectra corresponds to a different particular pattern of the same spectral fingerprint assigned to that group of spectra, associated with an imaged particle. Hereinafter, a pattern of a spectral fingerprint associated with a set of spectra is referred to as a 'spectral fingerprint pattern'. Thus, each group of spectra associated with a characteristic spectral fingerprint of the particle features a plurality of intra-particle spectral fingerprint patterns of the imaged particle.

Based on this newly determined sub-classification of the spectral imaging data, in general, and of the focus-fusion multi-layer spectral imaging data, in particular, it is possible to associate different spectral fingerprint patterns of the same particle with different intra-particle morphological regions varying in concentration and/or density of the chemically pure, but morphologically heterogeneous, particulate substance. Furthermore, it was determined by the inventors that shifts in spectral parameters, herein, also referred to as spectral shifts, present in a given group of intra-particle spectral fingerprint patterns of an individual particle are primarily due to local, intra-particle, variation or heterogeneity in particle morphology such as shape or geometry, and porosity, and, due to local, intra-particle, variation or heterogeneity in surface concentration and/or density of the chemically pure substance.

The novelty of the present invention is based on identifying shifts in spectral parameters, for example, emission wavelength and/or emission intensity or amplitude, present in classified spectral imaging spectral fingerprint data, in general, and on identifying shifts in spectral parameters in classified focus-fusion multi-layer spectral imaging spectral fingerprint data, in particular, and using the identified spectral shift data for revealing, correlating, and displaying intra-particle morphological and concentration/density data in the forms of intra-particle morphological concentration/density maps and histograms of the chemically pure particulate substance, which are representative of, and directly applicable to, intra-particle physicochemical analysis and characterization of a chemically pure particulate substance.

In Step 1 of the method for generating intra-particle morphological concentration/density maps and histograms of a chemically pure particulate substance, there is acquiring a set of spectral images, in general, and acquiring a set of focus-fusion multi-layer spectral images of one or more particle layers, in particular, by a spectral imaging system, for each of a number of particles of the chemically pure particulate substance having a plurality of particles.

In Step 2, there is performing pattern recognition classification analysis on the set of the acquired spectral images, in general, anid, on the set of the acquired focus-fusion multi-layer spectral images, in particular, for each of the number of imaged particles of the chemically pure particulate substance, for forming at least the same number of sets of single-particle spectral fingerprint data, where each set of single particle spectral fingerprint data is associated with a single particle. The plurality of sets of the single-particle spectral fingerprint data is stored in a single-particle scenario database.

Steps 1 and 2 are performed according to the previously surrrnarized prior art disclosures of U.S. patent application Ser. No. 09/322,975, U.S. patent application Ser. No. 09/146,361, U.S. Pat. No. 6,091,843, and U.S. Pat. No. 5,880,830, the teachings of each of which are incorporated by reference for all purposes as if fully set forth herein. For particularly understanding the present invention, the following description, referring to FIG. 1, based on the above referenced disclosures, is herein provided.

Figure 1:
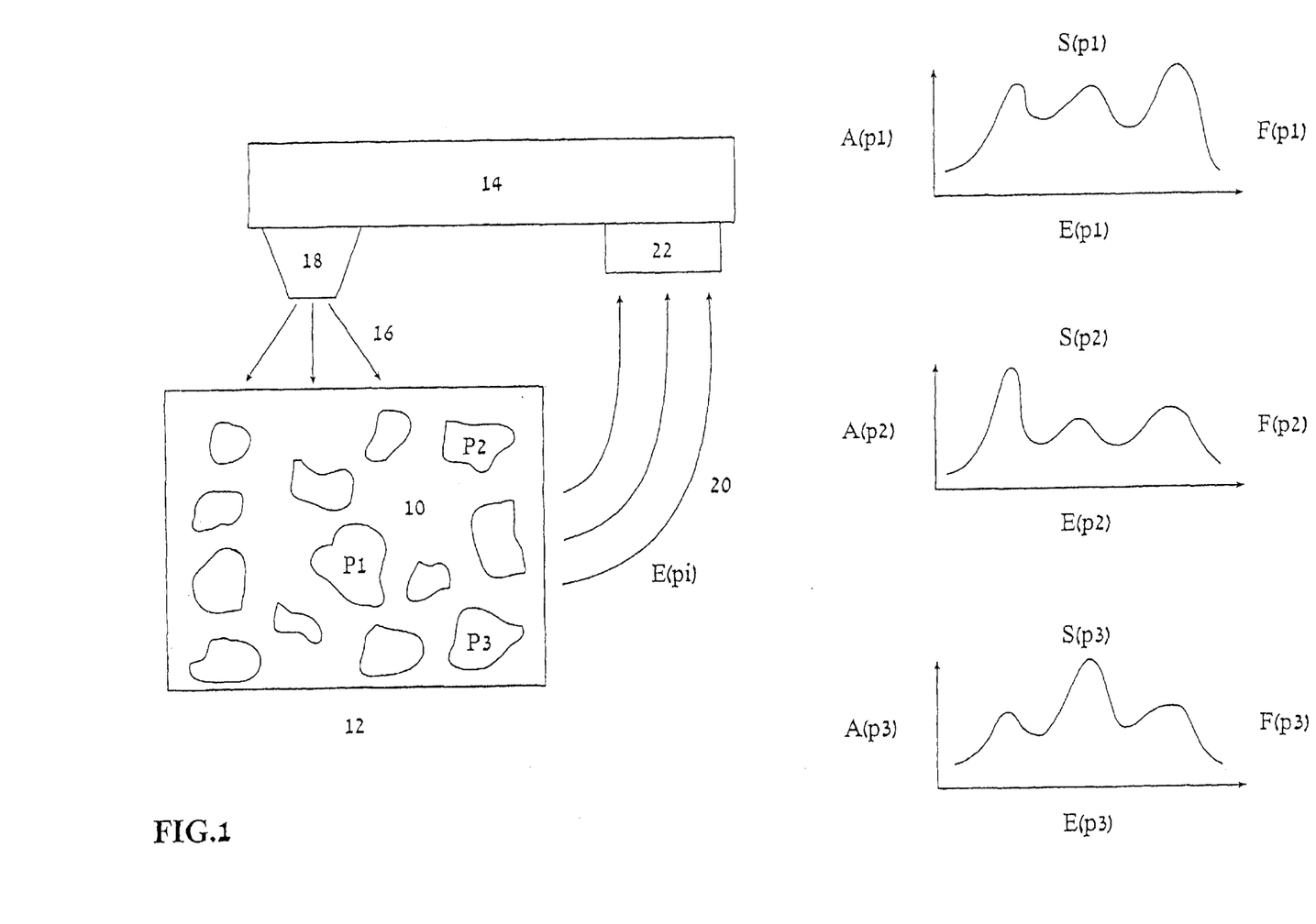
FIG. 1 is an illustration of spectral imaging, in general, and, focus-fusion multi-layer spectral imaging, in particular, of a chemically pure particulate substance featuring intra-particle heterogeneous morphology and regions of varying concentration/density, in accordance with the present invention.

Referring now to FIG. 1, an illustration of spectral imaging, in general, and, focus-fusion multi-layer spectral imaging, in particular, of a chemically pure particulate substance featuring intra-particle heterogeneous morphology and regions of varying concentration/density, chemically pure particulate substance 10, featuring a plurality of N individual particles, is positioned in an imaging sample holding device 12, part of spectral imaging system 14, where spectral imaging system 14 is operative for detecting, acquiring, measuring, processing, and displaying spectral imaging data and information, in general, and focus-fusion multi-layer spectral imaging data and information, in particular. Imaging source energy 16, preferably, but not limited to, electromagnetic radiation, supplied by imaging energy source 18, is incident upon substance 10, and is affected by any combination of absorption, reflection, transmission, diffraction, and/or scattering, mechanisms, by each imaged particle, $p_i$, for a number, n, of imaged particles, for i=1 to n, where n is less than or equal to N. Spectral imaging system 14 collects affected energy 20 by energy collector 22.

In substance 10, for each imaged particle, $p_i$, for example, $p_1$, $p_2$, and $p_3$, a set of spectral images, in general, and, a set of focus-fusion multi-layer spectral images, in particular, is acquired. Pattern recognition classification analysis is performed on each set of the acquired spectral images, in general, and, on each set of the focus-fusion multi-layer spectral images, in particular, for each imaged particle, $p_i$, of a number of imaged particles, for example, $p_1$, $p_2$, and $p_3$, for forming an equal number of sets of single-particle spectral fingerprint data, $F(p_i)$, for example, $F(p_1)$, $F(p_2)$, and $F(p_3)$, respectively, where each set of single-particle spectral fingerprint data is associated with a single imaged particle.

Each set of single-particle spectral fingerprint data, $F(p_i)$, is characterized by a single-particle spectral fingerprint spectrum, $S(p_i)$, featuring intensity or amplitude, $A(p_i)$, plotted as a function of affected energy, $E(p_i)$, 20 collected during imaging particle, $p_i$, by spectral imaging system 14. Preferably, affected energy, $E(p_i)$, 20 is expressed in terms of wavelength, frequency, or wavenumber, of electromagnetic radiation, such as fluorescent or phosphorescent light, emitted by an imaged particle, $p_i$. This data is stored in a single-particle scenario database. This process is clearly illustrated in FIG. 1, where each set of single-particle spectral fingerprint data, $F(p_1)$, $F(p_2)$, and $F(p_3)$, for each imaged particle $p_1$, $p_2$, and $p_3$, respectively, is characterized by a single-particle spectral fingerprint spectrum, $S(p_1)$, $S(p_2)$, and $S(p_3)$, respectively, referenced by 30, 32, and 34, respectively.

In Step 3, there is identifying at least one spectral shift, preferably, a plurality of spectral shifts, in each set of the single-particle spectral fingerprint data associated with a single particle, for forming an intra-particle region group featuring a plurality of sub-sets of intra-particle spectral fingerprint pattern data, where selected data elements in each sub-set are shifted relative to corresponding data elements in each remaining sub-set in the same intra-particle region group. This step represents the main, but not only, aspect of the novelty of the present invention.

This spectral shift identification step is performed for each of the number, n, imaged particles of the substance, for forming a plurality of intra-particle region groups of sub-sets of intra-particle spectral fingerprint pattern data, relating to the entire chemically pure particulate substance 10. This data is stored in an intra-particle scenario database.

In general, the identification procedure involves analyzing the plurality of spectral images for those particular spectral images which only slightly differ by relatively small shifts in the affected energy, $E(p_i)$, and/or, only slightly differ by relatively small shifts in the intensity or amplitude, $A(p_i)$, collected by spectral imaging system 14. Preferably, the identification procedure involves analyzing the plurality of spectral images for those particular spectral images which only slightly differ by relatively small shifts in the affected energy, $E(p_i)$, 20, in terms of a shift in wavelength, frequency, or, wavenumber, of fluorescent or phosphorescent light emitted by an imaged particle, $p_i$, and collected by spectral imaging system 14.

Specifically, there is identifying at least one spectral shift, $s_i$, in each set of single-particle spectral fingerprint data, $F(p_i)$, associated with an imaged particle, $p_i$, for forming an intra-particle region group, $RG(p_i)$, featuring a plurality of sub-sets of intra-particle spectral fingerprint pattern data, $FP(p_i, R_j)$, where selected data elements, for example, affected energy, $E(p_i)$, and/or, intensity or amplitude, $A(p_i)$, in each sub-set, $FP(p_i, R_j)$, are shifted relative to corresponding data elements in each remaining sub-set, $FP(p_i, R_k)$, for k not equal to j, in the same intra-particle region group, $RG(p_i)$.

Intra-particle region group sub-set identifier, $R_j$, for j=1 to J different sub-sets in each intra particle region group, is used for distinguishing among the plurality of sub-sets of intra-pazrticle spectral fingerprint pattern data, $FP(p_i, R_j)$, associated with the same set of single-particle spectral fingerprint data, $F(p_i)$. This classification enables performing Step 4 of forming a set of intra-particle morphological concentration/density data from each intra-particle region group, $RG(p_i)$, featuring the plurality of sub-sets of intra-particle spectral fingerprint pattern data, $FP(p_i, R_j)$.

Each sub-set of intra-particle spectral fingerprint pattern data, $FP(p_i, R_j)$, is characterized by an intra-particle spectral fingerprint pattern spectrum, $S(p_i, R_j)$, featuring intensity or amplitude, $A(p_i, R_j)$, plotted as a function of affected energy, $E(p_i, R_j)$, 20 collected during imaging particle, $p_i$, by spectral imaging system 14. This data is stored in an intra-particle scenario database.

Figure 2:
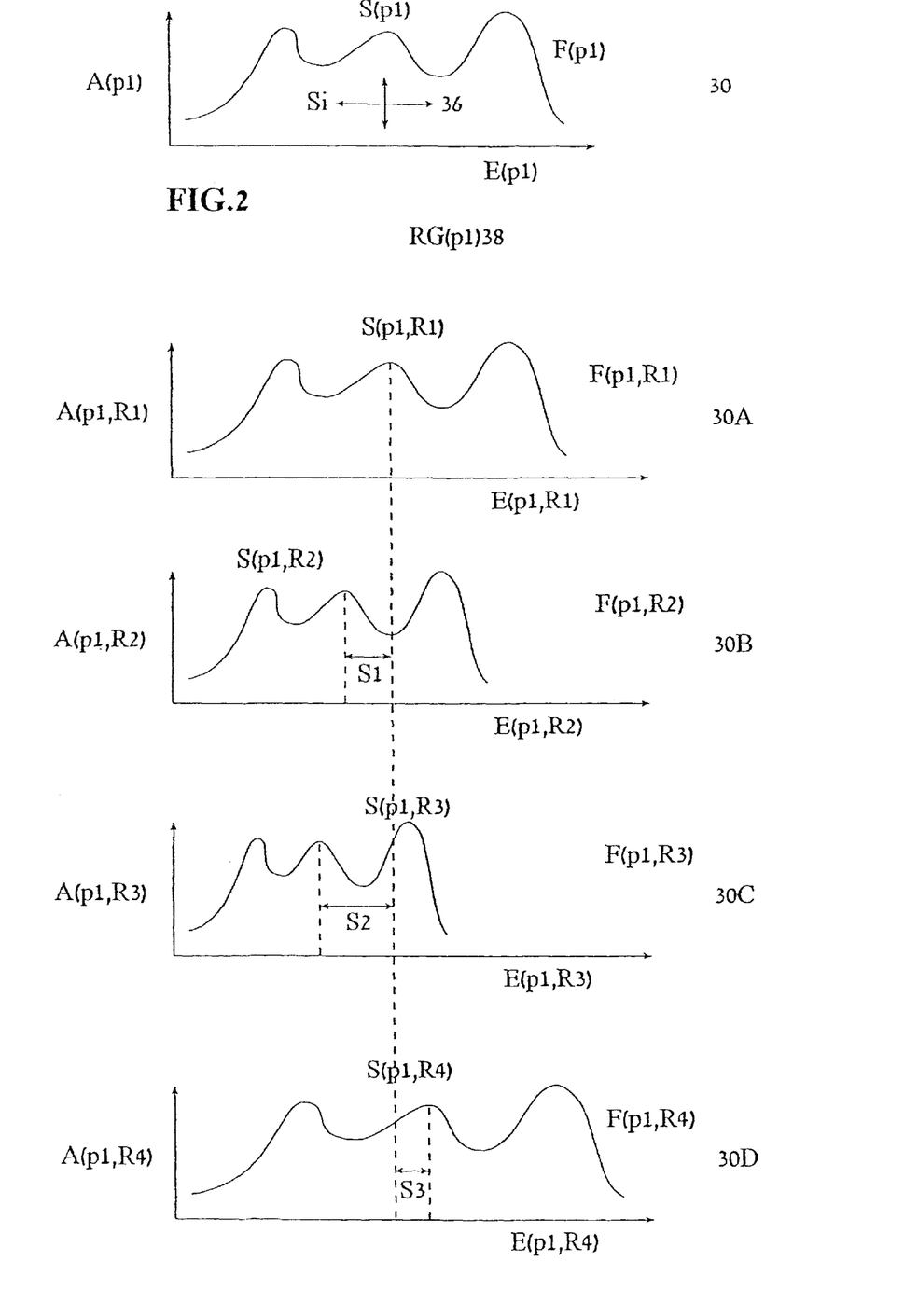
FIG. 2 is a schematic diagram illustrating the step of identifying spectral shifts in intra-particle spectral imaging data, in general, and, focus-fusion multi-layer spectral imaging data, in particular, in accordance with the present invention.

The above described process of identifying spectral shifts is clearly illustrated in FIG. 2, a schematic diagram illustrating the step of identifying spectral shifts in intra-particle spectral imaging data, in general, and, focus-fusion multi-layer spectral imaging data, in particular. For example, in the set of single-particle spectral fingerprint data, $F(p_1)$, 30 (from FIG. 1) associated with imaged particle, $p_1$, and characterized by single-particle spectral fingerprint spectrum, $S(p_1)$, there is identifying at least one spectral shift, $s_i$, of selected data elements, for example, affected energy, $E(p_i)$, and/or, intensity or amplitude, $A(p_i)$, where potentially identified spectral shifts, $s_i$, are referenced in FIG. 2 by the four directional crossed arrows 36, for forming intra-particle region group, $RG(p_1)$ 38. In this example, for imaged particle $p_1$, $RG(p_1)$ 38 features four sub-sets of intra-particle spectral fingerprint pattern data, $FP(p_1, R_1)$, $FP(p_1, R_2)$, $FP(p_1, R_3)$, and $FP(p_1, R_4)$, where each sub-set is characterized by a corresponding intra-particle spectral fingerprint pattern spectrum, $S(p_1, R_1)$, $S(p_1, R_2)$, $S(p_1, R_3)$, and $S(p_1, R_4)$, respectively, referenced by 30A, 30B, 30C, and 30D), respectively.

In FIG. 2, three spectral shifts, $s_1$, $s_2$, and, $s_3$, are shown identified, whereby selected data elements, for example, $E(p_1, R_j)$, in each sub-set, $FP(p_1, R_j)$, are shifted relative to corresponding data elements, $E(p_1, R_k)$, in each remaining sub-set, $FP(p_1, R_k)$, for k not equal to j, in the, same intra-particle region group, $RG(p_1)$ 36. In this particular example, the first sub-set of intra-particle spectral fingerprint pattern data, $FP(p_1, R_1)$, characterized by the corresponding intra-particle spectral fingerprint pattern spectrum, $S(p_1, R_1)$, referenced by 30A, is shown as a baseline used in identifying and illustrating the three spectral shifts, $S_1$, $S_2$, and, $S_3$, of selected data elements, in this case, $E(p_1, R_1)$, from corresponding data elements, in this case, $E(p_1, R_2)$, $E(p_1, R_3)$, and $E(p_1, R_4)$, respectively, in the three remaining sub-sets of intra-particle spectral fingerprint pattern data, $FP(p_1, R_2)$, $FP(p_1, R_3)$, and $FP(p_1, R_4)$, respectively, where each remaining sub-set is characterized by the corresponding intra-particle spectral fingerprint pattern spectrum, $S(p_1, R_2)$, $S(p_1, R_3)$, and $S(p_1, R_4)$, respectively, referenced by 30B, 30C, and 30D), respectively.

In Step 4, there is forming a set of intra-particle morphological concentration/density data, relating to each imaged particle of the chemically pure particulate substance, from each intra-particle region group featuring the plurality of sub-sets of intra-particle spectral fingerprint pattern data associated with a corresponding set of single-particle spectral fingerprint data.

For each imaged particle, the set of intra-particle morphological concentration/density data features a plurality of intra-particle morphological region types, where each intra-particle morphological region type is associated with a surface concentration value and a density value of the chemically pure substance. This step is performed for each of the number, n, imaged particles of the substance, for forming a plurality of sets of intra-particle morphological concentration/density data, relating to the entire chemically pure particulate substance 10. This data is stored in an intra-particle morphological concentration/density database.

Specifically, each imaged particle, $p_i$, of chemically pure particulate substance 10 being analyzed is considered morphologically heterogeneous, and features a plurality of intra-particle morphological region types, $R_j$, for j=1 to J different types of intra-particle morphological regions identified in, or assigned to, a particle, corresponding to the intra-particle region group sub-set identifier, $g_j$, used in Step 3 for distinguishing among the plurality of sub-sets of intra-particle spectral fingerprint pattern data, $FP(p_i, R_j)$, associated with the same set of single-particle spectral fingerprint data, $F(p_i)$.

Each intra-p article morphological region type, $R_j$, is associated with a surface concentration value, $SC(R_j)$, and a density value, $D(R_j)$, of the chemically pure substance making up each imaged particle, $p_i$, where $SC(R_j)$, and $D(R_j)$ vary throughout each imaged particle, $p_i$. Due to this local, intra-particle, variation or heterogeneity in particle morphology such as shape or geometry and porosity, and, due to local, intra-particle, variation or heterogeneity in surface concentration and/or density of the chermically pure substance of imaged particle, $p_i$, incident energy 16 is affected differently by each intra-particle morphological region type, $R_j$. This physicochernical phenomenon during imaging particles of chemically pure particulate substance 10, enables forming intra-particle region group, $RG(p_i)$, in Step 3, featuring the plurality of sub-sets of intra-particle spectral fingerprint pattern data, $FP(p_i, R_j)$, where selected data elements in each sub-set, $FP(p_i, R_j)$, are shifted relative to corresponding data elements in each remaining sub-set, $FP(p_i, R_k)$, for k not equal to j, in the same intra-particle region group, $RG(p_i)$.

Values of $SC(R_j)$, and $D(R_j)$ are obtained by relating the spectral imaging data, in general, and by relating the focus-fusion multi-layer spectral imaging data, in particular, in each intra-particle region group, $RG(p_i)$, obtained and stored from imaging the sample of chemically pure particulate substance, to empirically determined spectral imaging data in a standard intra-particle region group, $RG(p_i)_s$, obtained and stored from imaging a standard sample of a chemically pure particulate substance featuring known local, intra-particle, variation or heterogeneity in particle morphology such as shape or geometry and porosity, and, known local, intra-particle, variation or heterogeneity in surface concentration and/or density of the chemically pure substance of the standard sample.

Figure 3:
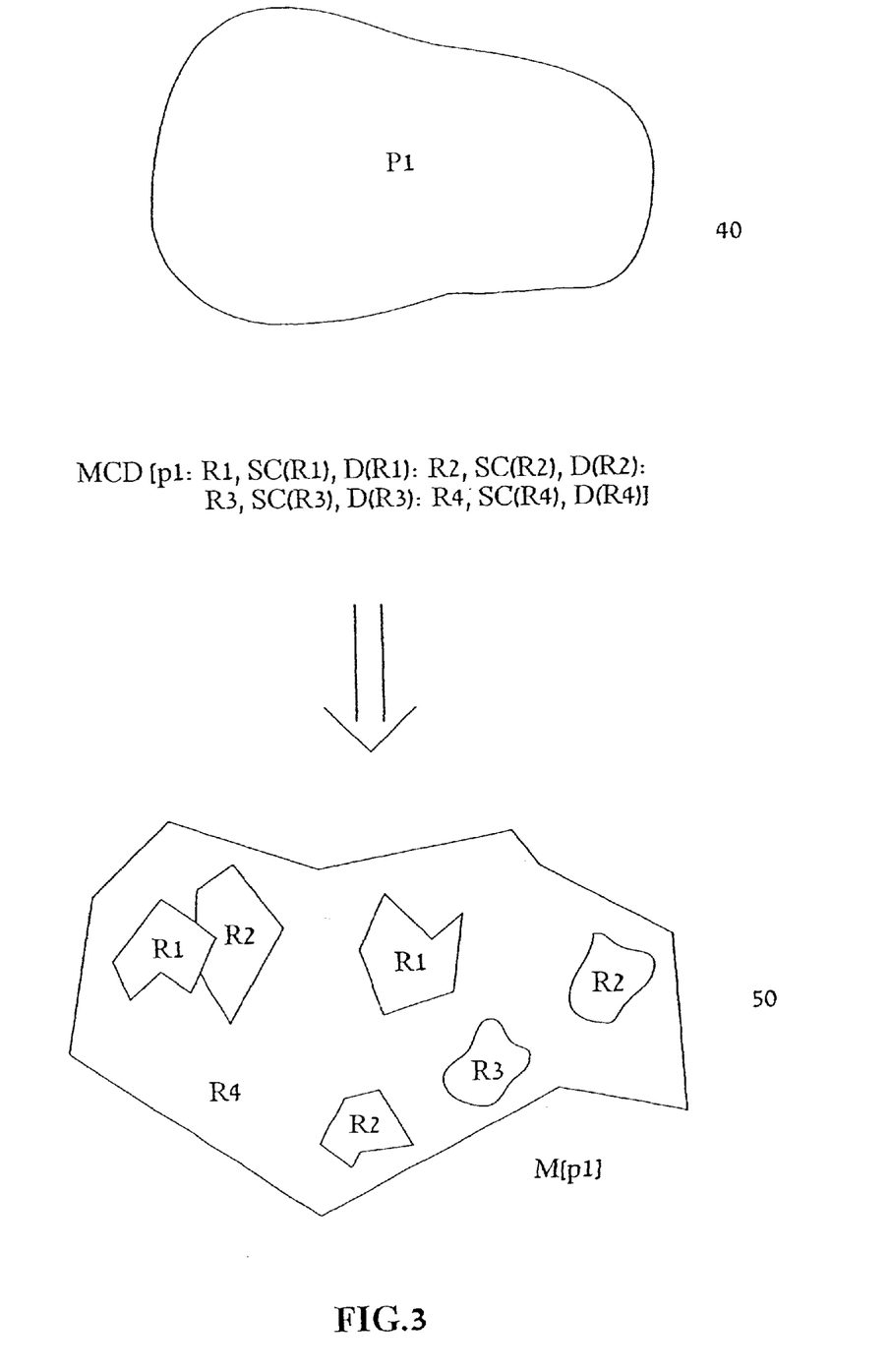
FIG. 3 is a schematic diagram illustrating an intra-particle morphological concentration/density map of a particle, generated from the exemplary set of intra-particle morphological concentration/density data formed from the results of FIG. 2, in accordance with the present invention.

Accordingly, for each imaged particle, $p_i$, the set of intra-particle morphological concentration/density data is referred to as $MCD[p_i: R_j, SC(R_j), D(R_j)]$, for j=1 to J different types of intra-particle morphological regions. For example, for imaged particle $p_1$, the set of intra-particle morphological concentration/density data is written as: $MCD[p_1: R_j, SC(R_j), D(R_j)]$, for j=1 to 4. $SC(R_j)$ and $D(R_j)$, for j=1 to 4, are evaluated from the four sub-sets of intra-particle spectral fingerprint pattern data, $FP(p_1, R_1)$, $FP(p_1, R_2)$, $FP(p_1, R_3)$, and $FP(p_1, R_4)$, respectively, where each sub-set is characterized by the corresponding intra-particle spectral fingerprint pattern spectrum, $S(p_1, R_1)$, $S(p_1, R_2)$, $S(p_1, R_3)$, and $S(p_1, R_4)$, respectively, and associated with four corresponding different intra-particle morphological region types, $R_1, R_2, R_3$, and $R_4$. Thus, referring to FIG. 3, for imaged particle, $p_1$, the complete set of intra-particle morphological concentration/density data becomes: $MCD[p_1: R_1, SC(R_1), D(R_1); R_2, SC(R_2), D(R_2); R_3, SC(R_3), D(R_3); R_4, SC(R_4), D(R_4)]$, referenced by 40.

In Step 5, there is generating an in tra-particle morphological concentration/density map from each set of intra-particle morphological conceritration/density data, for illustrating local, intra-particle, morphological distribution of concentration and density of the chemically pure substance throughout the particle associated with that set of intra-particle morphological concentration/density data.

This step is performed for each of a number, n, imaged particles of the substance, for generating n morphological concentration/density maps, relating to the chemically pure particulate substance 10. Each morphological concentration/density map is stored in an intra-particle morphological concentration/density map database.

Specifically, for each imaged particle, $p_i$, of chemically pure particulate substance 10 being analyzed, there is generating an intra-particle morphological concentration/density map, $M[p_i]$, from each set of intra-particle morphological concentration/density data, $MCD[p_i: R_j, SC(R_j), D(R_j)]$, for j=1 to J, featuring J different Apes of intra-particle morphological regions, where each intra-particle morphological region type, $R_j$, is associated with a surface concentration value, $SC(R_j)$, and a density value, $D(R_j)$, of the chemically pure substance.

Referring again to FIG. 3, for imaged particle, $p_1$, having the set of intra-particle morphological concentration/density data, $MCD[p_1: R_1, SC(R_1), D(R_1); R_2, SC(R_2), D(R_2); R_3, SC(R_3), D(R_3); R_4, SC(R_4), D(R_4)]$ 40, formed and assigned values according to previously described Step 4 above, there is generating intra-particle morphological concentration/density map, $M[p_1]$ 50.

In Step 6, there is generating a morphological concentration/density histogram, or frequency distribution, from the plurality of sets of the intra-particle morphological concentration/density data, for illustrating a statistically based global morphological distribution of surface concentration and density throughout the entire chemically pure particulate sample.

This step is performed using the previously obtained data sets of the number, n, imaged particles of the substance, for generating the morphological concentration/density histogram, relating to and representative of the entire chemically pure particulate substance 10. Each histogram is stored in a morphological concentration/density histogram database.

Specifically, using the previously obtained data sets of the n imaged particles, $p_i$, for i =1 to n, making up sample number, $(sample)_n$, of chemically pure particulate substance 10 being analyzed, there is generating a morphological concentration/density histogram, $H[(sample)_n]$, from the plurality of sets of intra-particle morphological concentration/density data, $MCD[p_i: R_j, SC(R_j), D(R_j)]$, for i=1 to n, and j=1 to J, for each particle number, i, and for J different types of intra-particle morphological regions, where J can vary among the imaged particles.

Figure 4:
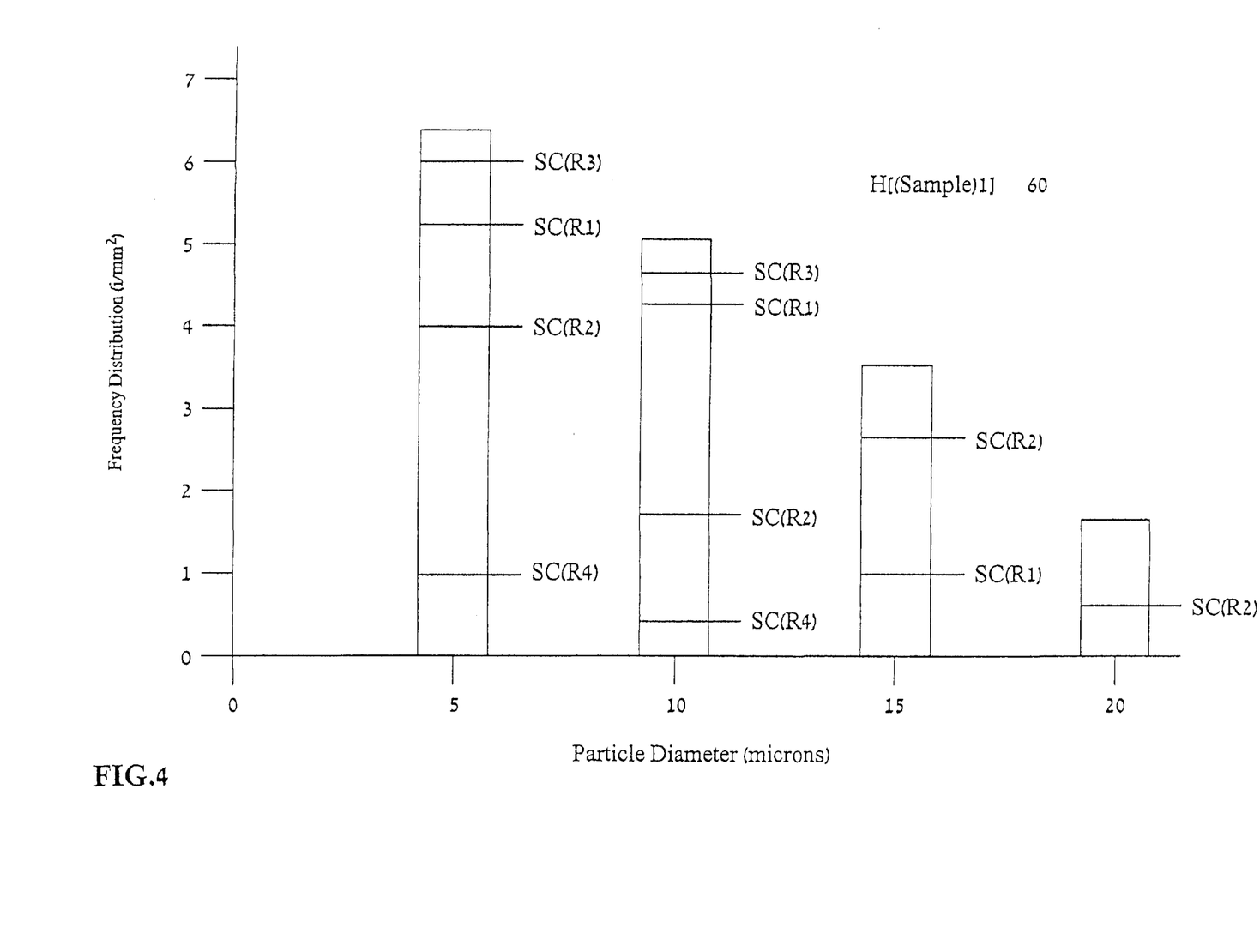
FIG. 4 is a schematic diagram illustrating a morphological concentration/density histogram generated from a plurality of sets of intra-particle morphological concentration/density map data, corresponding to a statistically based global morphological distribution of concentration of the chemically pure substance throughout the entire multi-particle sample, in accordance with the present invention.

For example, referring to FIG. 4, a schematic diagram illustrating a morphological concentration/density histogram generated from a plurality of sets of intra-particle morphological concentration/density map data, from the data sets of the n imaged particles of $(sample)_1$ representative of substance 10, morphological concentration/density histogram, $H[(sample)_1]$ 60, is generated from the plurality of sets of intra-particle morphological concentration/density data, $MCD[p_i: R_j, SC(R_j), D(R_j)]$, for i=1 to n, and j=1 to J, for each particle number, i, corresponding to a statistical morphological distribution of a plurality of individual particles of chemically pure particulate substance 10. Morphological concentration/density histogram, $H[(sample)_1]$ 60, features a graphical plot of the statistical distribution of the surface concentration, $SC(R_j)$, of the chemically pure substance in each intra-particle morphological region type, $R_j$, as a function of particle diameter (microns), among the plurality of particles of substance 10. For illustrative purposes, four intra-particle morphological region types, $R_1$, $R_2$, $R_3$, and $R_4$, each with a corresponding intra-particle surface concentration, $SC(R_1)$, $SC(R_2)$, $SC(R_3)$, and $SC(R_4)$, respectively, are shown in morphological concentration/density histogram, $H[(sample)_1]$ 60.

While the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for generating intra-particle morphological concentration/density maps and histograms of a chemically pure particulate substance, comprising the steps of:
   (a) acquiring a set of spectral images by a spectral imaging system for each of a number of particles of the chemically pure particulate substance having a plurality of said particles;
   (b) performing pattern recognition classification analysis on each said set of said acquired spectral images for each said imaged particle, for forming a number of sets of single-particle spectral fingerprint data;
   (c) identifying at least one spectral shift in each said set of single-particle spectral fingerprint data associated with each said imaged particle, for forming an intra-particle region group featuring a plurality of sub-sets of intra-particle spectral fingerprint pattern data, where selected data elements in each said sub-set are shifted relative to corresponding said data elements in each remaining said sub-set in same said intra-particle region group;
   (d) forming a set of intra-particle morphological concentration/density data relating to each said imaged particle from each said intra-particle region group;
   (e) generating each of the intra-particle morphological concentration/density maps from each said set of said intra-particle morphological concentration/density data; and
   (f) generating each of the morphological concentration/density histograms from a plurality of said sets of said intra-particle morphological concentration/density data, for illustrating a statistically based global morphological distribution of surface concentration and density throughout the chemically pure particulate substance.

2. The method of claim 1, wherein the chemically pure particulate substance features at least one chemically pure compound.

3. The method of claim 1, wherein the chemically pure particulate substance is selected from the group consisting of a powder, a powder mixture, a medicinal powder featuring at least one active ingredient and at least one inactive ingredient, a frozen suspension of a powder, and a biological specimen.

4. The method of claim 1, wherein the chemically pure particulate substance features intra-particle heterogeneous morphology and regions of varying concentration and density.

5. The method of claim 1, wherein physicochemical properties and characteristics of said particles are selected from the group consisting of independent of particle depth and dependent of particle depth.

6. The method of claim 1, wherein step (a) said spectral images are focus-fusion multi-layer spectral images acquired by focus-fusion multi-layer spectral imaging of said particles of the chemically pure particulate substance.

7. The method of claim 1, wherein step (a) said spectral imaging system includes an imaging energy source supplying imaging source energy incident upon the chemically pure particulate substance, said imaging source energy is affected by said imaged particles by at least one mechanism selected from the group consisting of absorption, reflection, transmission, diffraction, scattering, fluorescence, and phosphorescence.

8. The method of claim 1, whereby each said set of single-particle spectral fingerprint data is characterized by a single particle spectral fingerprint spectrum featuring intensity or ampplitude plotted as a function of incident imaging energy affected by a said imaged particle and collected during imaging said particle by said spectral imaging system.

9. The method of claim 8, whereby said affected energy is expressed in a term selected from the group consisting of wavelength, frequency, and, wavenumber, of electromagnetic radiation emitted by said imaged particle.

10. The method of claim 1, wherein step (c) said identifying said at least one spectral shift is performed for each said imaged particle of the chemically pure substance, for forming a plurality of said intra-particle region groups of said sub-sets of said intra-particle spectral fingerprint pattern data relating to the entire chemically pure particulate substance.

11. The method of claim 1, wherein step (c) said selected data elements of said sub-sets of said intra-particle spectral fingerprint pattern data are selected from the group consisting of incident imaging energy affected by a said imaged particle and amplitude of said incident imaging energy affected by said imaged particle.

12. The method of claim 1, wherein step (c) said selected data elements of said sub-sets of said intra-particle spectral fingerprint pattern data are incident imaging energy affected by a said imaged particle.

13. The method of claim 1, wherein step (c) each said sub-set of said intra-particle spectral fingerprint pattern data is characterized byan intra-particle spectral fingerprint pattern spectrum featuring intensity or amplitude plotted as a fraction of incident imaging energy affected by a said imaged particle.

14. The method of claim 1, whereby for each said imaged particle, said set of said intra-particle morphological concentration/density data features a plurality of intra-particle morphological region types, where each said intra-particle morphological region type is associated with a different:value of said surface concentration and a different value of said density of the chemically pure particulate substance.

15. A method for identifying intra-particle morphological distribution of surface concentration and density of a chemically pure particulate substance, comprising the steps of:
   (a) acquiring a set of spectral images by a spectral imaging system for each of a number of particles of the chemically pure particulate substance having a plurality of said particles;

(b) performing pattern recognition classification analysis on each said set of said acquired spectral images for each said imaged particle, for forming a number of sets of single-particle spectral fingerprint data;

(c) identifying at least one spectral shift in each said set of single-particle spectral fingerprint data associated with each said imaged particle, for forming an intra-particle region group featuring a plurality of sub-sets of intra-particle spectral fingerprint pattern data, where selected data elements in each said sub-set are shifted relative to corresponding said data elements in each remaining said sub-set in same said intra-particle region group;

(d) forming a set of intra-particle morphological concentration/density data relating to each said imaged particle from each said intra-particle region group; and (e) forming a plurality of intra-particle morphological region types from each said set of said intra-particle morphological concentration/density data, where each said intra-particle morphological region type is associated with a different value of the surface concentration and a different value of the density of the chemically pure particulate substance, thereby identifying the intra-particle morphological distribution of the surface concentration and density of the chemically pure particulate substance.

16. The method of claim 15, wherein the chemically pure particulate substance features at least one chemically pure compound.

17. The method of claim 15, wherein the chemically pure particulate substance is selected from the group consisting of a powder, a powder mixture, a medicinal powder featuring at least one active ingredient and at least one inactive ingredient, a frozen suspension of a powder, and a biological specimen.

18. The method of claim 15, wherein the chemically pure particulate substance features intra-particle heterogeneous morphology and regions of varying concentration and density.

19. The method of claim 15, wherein physicochemical properties and characteristics of said particles are selected from the group consisting of independent of particle depth and dependent of particle depth.

20. The method of claim 15, wherein step (a) said spectral images are focus-fusion multi-layer spectral images acquired by focus-fusion multi-layer spectral imaging of said particles of the chemically pure particulate substance.

21. The method of claim 15, wherein step (a) said spectral imaging system includes an imaging energy source supplying imaging source energy incident upon the chemically pure particulate substance, said imaging source energy is affected by said imaged particles by at least one mechanism selected from the group consisting of absorption, reflection, transmission, diffraction, scattering, fluorescence, and phosphorescence.

22. The method of claim 15, whereby each said set of single-particle spectral fingerprint data is characterized by a single-particle spectral fingerprint spectrum featuring intensity or amplitude plotted as a function of incident imaging energy affected by a said imaged particle and collected during imaging said particle by said spectral imaging system.

23. The method of claim 22, whereby said affected energy is expressed in a term selected from the group consisting of wavelength, frequency, and, wavenumber, of electromagnetic radiation emitted by said imaged particle.

24. The method of claim 15, wherein step (c) said identifying said at least one spectral shift is-perfoimed for each said imaged particle of the chemically pure substance, for forming a plurality of said intra-particle region groups of said sub-sets of said intra-particle spectral fingerprint pattern data relating to the entire chemically pure particulate substance.

25. The method of claim 15, wherein, step (c) said selected data elements of said sub-sets of said intra-particle spectral fingerprint pattern data are selected from the group consisting of incident imaging energy affected by a said imaged particle and amplitude of said incident imaging energy affected by said imaged particle.

26. The method of claim 15, wherein step (c) said selected data elements of said sub-sets of said intra-particle spectral fingerprint pattern data are incident imaging energy affected by a said imaged particle.

27. The method of claim 15, wherein step (c) each said sub-set of said intra-particle spectral fingerprint pattern data is characterized by an intra-particle spectral fingerprint pattern spectrum featuring intensity or amplitude plotted as a function of incident imaging energy affected by a said imaged particle.

* * * * *